United States Patent [19]

Dorman et al.

[11] Patent Number: 4,718,893
[45] Date of Patent: Jan. 12, 1988

[54] PRESSURE REGULATED IMPLANTABLE INFUSION PUMP

[75] Inventors: Frank D. Dorman; Henry Buchwald, both of Minneapolis, Minn.

[73] Assignee: University of Minnesota, St. Paul, Minn.

[21] Appl. No.: 825,246

[22] Filed: Feb. 3, 1986

[51] Int. Cl.[4] .............................................. A61M 5/14
[52] U.S. Cl. ..................................... 604/67; 604/151; 604/891.1; 604/134; 128/DIG. 12; 417/473
[58] Field of Search ............... 604/131, 132, 141, 134, 604/151, 153, 891, 67; 128/DIG. 12, DIG. 13; 92/37, 39; 60/533, 583; 417/472, 473; 222/52, 55, 386.5

[56] References Cited

U.S. PATENT DOCUMENTS

| | | |
|---|---|---|
| 2,815,152 | 12/1957 | Mills . |
| 2,947,470 | 8/1960 | Ruben et al. . |
| 3,023,750 | 3/1962 | Baron . |
| 3,731,681 | 5/1973 | Blackshear et al. . |
| 3,951,147 | 4/1976 | Tucker et al. . |
| 4,056,095 | 11/1977 | Rey et al. . |
| 4,299,220 | 11/1981 | Dorman . |
| 4,373,527 | 2/1983 | Fischell . |
| 4,447,224 | 5/1984 | De Cant, Jr. et al. ................ 604/67 |
| 4,487,603 | 12/1984 | Harris . |
| 4,557,726 | 12/1985 | Reincke ...................... 128/DIG. 12 |

FOREIGN PATENT DOCUMENTS 1314002 11/1962 France .

OTHER PUBLICATIONS

Implantable Infusion Pumps, Buchwald and Rohde, Department of Surgery, University of Minnesota, ©1984, Year Book Medical Publishers, Inc., pp. 177-221.

Implantable Drug Infusion Devices, *Surgical Rounds*, Buchwald and Rohde, Department of Surgery, University of Minnesota, Jul. 1984, pp. 16-23.

*Primary Examiner*—Stephen C. Pellegrino
*Attorney, Agent, or Firm*—Merchant, Gould, Smith, Edell, Welter & Schmidt

[57] ABSTRACT

An implantable infusion pump (20) for infusing drugs or other chemical or solutions into the body. A movable diaphragm (26) forming a variable volume drug chamber (22). A fluid piston (32) opposing the force exerted by the diaphragm (26) on the drug solution in the drug chamber (22). The pressure of the fluid piston (32) being controlled by a regulator (33) providing a reference pressure and in fluid communication with the fluid piston (32). The regulator (33) reducing the fluid pressure of the piston fluid (32) as drug solution is expelled from the drug chamber (22) so as to maintain a constant pressure differential between the drug chamber (22) and an infusion site in the body. The implantable infusion pump (20) being readily adaptable to variable or electronic flow control.

16 Claims, 9 Drawing Figures

PRESSURE REGULATED IMPLANTABLE INFUSION PUMP

BACKGROUND OF THE INVENTION

The present invention relates to an implantable infusion pump. More particularly, the present invention relates to an implantable infusion pump which includes a pressure regulator apparatus for producing a constant drive pressure from a more variable driving force exerted on a drug solution contained in a variable volume drug chamber of the implantable infusion pump.

Infusion pump designs rarely appeared in the medical literature until the 1950s. Most of these early infusion pumps were extracorporeal. One such device included a reciprocating air pump driven by an electric motor. Yet another design considered comprised a metal housing for a glass syringe and a compression chamber fed by a tank of nitrogen gas. Yet another such infusion pump included a motorized syringe pump which included an electric motor connected to the worm drive that moved a syringe plunger by a gear box. The gears were interchangeable such that replacement of the gears permitted different delivery rates. Yet another infusion pump included a syringe plunger driven by a rider on a threaded shaft. Numerous other designs were considered for these extracorporeal infusion pumps. P. D. W. Soden in his thesis entitled "A Methodical Design Study of Miniature Profusion Devices For Chemotherapy of Cancer of the Head and Neck", studied possible designs for producing a miniature profusion device to be carried by ambulating patients receiving chemotherapeutic treatment for cancer of the head and neck. Quoting from his thesis, "Approximately two million alternative design solutions were synthesized and recorded in compact matrix form on a 'morphological chart'". One of the numerous design concepts mentioned by Soden for possible use with an extracorporeal infusion pump was the use of a small tubular arrangement containing an elastic metal bellows possibly constructed from preloaded disks so as to form a relatively small diaphragm in the tubular arrangement for exerting a fairly constant force on the drug solution being infused. Due to the size of the diaphram, this design provided for very little, if any, compensation for changes in atmostpheric pressure.

One of the earliest implantable infusion pumps intended for use in laboratory animals comprised a microinjector comprising a compressed spring held away from a rubber-capped glass tube by a metal alloy disk with a low melting point. Admisistration of the injection was accomplished by placing the animal near the coils of high-frequency induction heater. Activation of the coils melted the alloy disk and the spring ejected infusate into the desired site in the animal. A second implantable infusion pump for the continuous infusion of drugs utilized the osmotic pressure developed by a saturated aqueous solution of Congo red dye against water as its power source. The infusion pump comprised a partially collapsed rubber compartment filled with Congo red dye separated from a second water compartment by a semi-permeable cellophane member. Expansion of the rubber compartment as the water moved by osmosis into the Conge red solution ejected the drug from the infusion pump.

Implantable infusion pumps were clinically introduced in 1975. Implantable infusion pumps currently in clinical use or in animal trials anticipating clinical studies in the near future, include vapor pressure powered pumps, peristaltic pumps, and pulsatile solenoid pumps. The vapor pressure powered pump was developed at the University of Minnesota and is described hereafter. The peristaltic pump generally comprises a flexible tube placed in a U-shaped chamber in contact with rollers that press against the tube with sufficient force to occlude the tube's lumen. The rollers are rotated by a motor. As the rotor turns and the rollers compress the lumen of the tube, fluid is moved toward an exit. The rollers and housing are arranged so that a second roller begins to squeeze the tube before the first disengaged, preventing backflow of the infusate. Sandia Laboratories, Siemens AG, and Medtronic, Inc. have developed implantable pumps with peristaltic pumping mechanisms. A pulsatile solenoid pump includes a solenoid driven reciprocating chamber with two check valves to move infusate from the reservoir out through the delivery catheter. Infusate is stored in a flexible metal diaphragm reservoir. Such a pump has been developed by Fischell and colleagues at Johns Hopkins University Applied Physics Laboratory and by the Pacesetter Corporation.

Much effort has been expended in developing external infusion devices which provide a steady pressure on the drug solution so as to provide a steady flow of drug solution to the patient. For example, U.S. Pat. Nos. 2,815,152 and 3,023,750 as well as French Pat. No. 1,314,002 are examples of such devices.

Currently available implantable infusion pumps also have difficulty in maintaining constant pressure as the volume of the drug solution in their drug chambers changes. Typically, the output flow of drug solution is regulated by external means, an example of which is illustrated in U.S. Pat. No. 4,299,220, or if passive flow restrictions are used to control the drug solution output, flow variation must be tolerated. The two ambient conditions that commonly cause flow variation are temperature and atmospheric pressure. In the vapor-pressure powered infusion pump disclosed in U.S. Pat. No. 3,731,681, both of these conditions cause the pressure differential between the drug chamber and the internal body pressure to change thereby causing a corresponding change in drug solution flow rate from the infusion pump into an infusion site in the body. In addition, the spring action of the metal bellows typically used to separate the drug solution from the two-phase fluid adds a variable force to the otherwise volume independent force exerted by the vapor pressure, thereby causing a steady, although predictable decline in flow rates as the drug chamber empties.

In many applications it is necessary to change the flow rate of the drug solution frequently, more frequently than can be done by changing the concentration by an empty-refill cycle on a constant flow rate infusion pump. Examples of such applications are: (1) the delivery of insulin to a brittle diabetic with no residual insulin production, (2) the delivery of a chemotherapeutic agent that has a strong dependence on biological timing, or (3) the delivery of a hormone that is timed to the natural rhythm of the body.

Infusion pumps; for example, U.S. Pat. Nos. 4,373,527 and 4,146,029, have been developed which utilize electronic controls that respond to transmitted electromagnetic signals and thus can be programed by a non-invasive procedure. The electronics in these infusion pumps work relatively well due to the availability of very complex, low powered integrated circuits. However, such infusion pumps have complex flow control components that must respond to the electronic signals. An approach commonly used is to have the flow control device provide an impulse of drug solution flow for every impulse of electrical signal from the electronic control circuit. By having very small (microliter) individual impulses and repeating them within the normal clearance time of an infused drug solution in the blood stream (e.g. one to ten minutes), an approximation of steady flow is obtained. This method is very flexible in that both steady flow and variable flow up to bolus doses can be delivered by a single flow control mechanism. However, the high cycle rate of the flow control mechanism increases the wear rate of the components, increases power losses in start and stop events, and increases probability of failure of some component. If a particular component has a finite failure rate per cycle, the mean time to failure decreases as the rate of cycling goes up. When a repeatedly cycled valve is used to produce a constant flow rate for an extended time period (several hours) there is an unnecessary hazard involved that would not be present if the same fixed flow rate were achieved by other means. If the fixed flow rate were known, a simple capillary tube could deliver that rate with only one cycle of valve open and fixed dose, rather than a hundred or so open dose cycles which might be required in an electronic impulse controlled system.

Typical systems employed in such electronically controlled infusion pumps include: (a) cyclic filling and emptying of a small drug accumulator with upstream and downstream valves; (b) an active piston pump with passive valves; and (c) miniature roller (peristaltic) pumps. In all three of these mechanisms, the drug solution storage chamber is passive and is held at a fixed pressure usually a little above atmospheric pressure in order to suppress bubble formation from dissolved air. The low pressure serves to reduce the potential hazard of an infusator leak. Accumulator systems use a higher drug chamber pressure to get positive filling cycles.

The above described electronically controlled infusion pumps have an unnecessarily wide dynamic range and response time for many applications. Moreover, they are complex, expensive and subject to failure. On the other hand, the fixed flow rate unfusion pump has been shown to provide adequate therapy for a range of disease states with no flow control for a given cycle. An infusion pump is required which provides a degree of drug solution flow control which is better than currently available infusion pumps of the constant flow design but which is less complex than that of the presently available electronically controlled unfusion pumps.

The present invention solves these and many other problems associated with currently existing infusion pumps.

SUMMARY OF THE INVENTION

The present invention relates to an apparatus and method for controlling the pressure applied to a drug solution in the drug chamber of an implantable infusion pump.

The preferred embodiment of the present invention utilizes a pressurized support piston and pressure regulator arrangement to produce a constanc force (drive pressure) on a drug solution in the drug chamber from a more variable driving force that might be a spring mechanism or any other force producing device. Moreover, the pressure can be maintained without subjecting the drug solution to the high shear force at the exit port of the pressure regulator.

A preferred embodiment of the present invention readily lends itself to electronic control whereby the flow rate of the drug solution can be changed by transmitted electromagnetic signals. Moreover, the electronic control can be preprogrammed to vary the drug solution flow rate as required.

The present invention provides an electronically controlled infusion pump which is less complex than existing, electronically controlled infusion pumps. In an electronically controlled embodiment of the present invention, telemetry can be used either to directly set the reference pressure of the infusion pump's regulator by supplying telemetered power to an otherwise passive motor control circuit or provide commands to an electronic timing circuit that can execute the command at a later time using internal battery power. Many applications of the infusion pump of the present invention will require only a non-invasive method of resetting the drug solution flow rate and maintaining the flow rate until the next cycle time. An example of this might include most insulin delivery systems where the increase in flow rate to adjust for mealtime demand is done by the patient on his/her own schedule (e.g. at night the insulin flow rate is typically reduced to adjust for the lower demand during sleep). In applications where drug solution is delivered on a fixed variable rate schedule, such as in the case of hormone or chemotherapeutic agents, the infusion pump of the present invention can be preprogrammed and not require any intervention by the patient.

The preferred embodiment of the present invention has a variable volume drug chamber formed partially by a movable, relatively rigid diaphragm which moves under the influence of a force producing device to expell the drug solution from the drug chamber. Movement of the diaphragm is opposed by a column of pressurized fluid, herein referred to as a support piston, whose pressure is controlled by the reference pressure of a pressure regulator apparatus so as to allow only a constant force to be applied by the diaphragm on the drug solution in the drug chamber. Any excess force exerted by the diaphragm is absorbed by the support piston. The reference pressure of the regulator is interconnected to the support piston by a one-way flow valve which regulates fluid flow from the support piston to a reference pressure chamber of the regulator. In the preferred embodiment, the regulator need only release fluid from the support piston at a controlled rate in order to maintain constant drug solution pressure.

In some embodiments of the present invention, the reference pressure of the regulator will be preselected by appropriate configuration of a force producing device such as a spring device which acts on a diaphragm of the regulator so as to produce the regulator reference pressure.

In various embodiments of the present invention, the pressure regulator can maintain either an absolute internal drug chamber pressure or a relative internal drug chamber pressure wherein the regulator compensates for atmospheric pressure so as to maintain a constant pressure differential between the drug chamber and the internal body pressure.

In various embodiments of the present invention, the support piston will utilize a closed system wherein its operating fluid is kept separate from the drug solution or an open system wherein the drug solution itself is used as the operating fluid of the support piston.

An advantage of the regulator of the present invention is that power is required only to change the reference pressure of the regulator in order to change the drug solution flow rate. The actual work needed to deliver the drug solution at the selected flow rate is accomplished by the pressure of the drug chamber. The pressure of the drug chamber can be readily varied by changing the reference pressure of the regulator since the drug chamber pressure is the difference between the total force being exerted by the drug chamber diaphragm and the countering force of the support piston whose pressure is controlled by the reference pressure of the regulator. In the preferred embodiment, to reduce drug chamber pressure, the regulator decreases the outflow of fluid from the support piston. In order to increase the drug chamber pressure, the fluid in the support piston is released more rapidly by the regulator. Accordingly, the regulator need only vary the flow of fluid out of the support piston in order to vary drug chamber pressure.

An advantage of the present invention is that by using a variable drug chamber pressure design, much of the safety and ease of use of the steady flow infusion pump designs is retained.

An electronically controlled embodiment of the present invention might use an electromechanical arrangement to compress or expand the regulator diaphragm in order to vary the reference pressure of the regulator.

These and various other advantages and features of novelty which characterize the present invention are pointed out with particularity in the claims and next hereto and forming a part hereof. However, for a better understanding of the invention, its advantages and objects obtained by its use, reference should be had to the drawings which form a further part hereof and to the accompanying descriptive matter in which there is illustrated and described a preferred embodiment of the present invention.

BRIEF DESCRIPTION OF THE DRAWINGS

In the drawings, in which like reference numerals and letters indicate corresponding part throughout the several views.

DETAILED DESCRIPTION OF A PREFERRED EMBODIMENT OF THE PRESENT INVENTION

Figure 1:
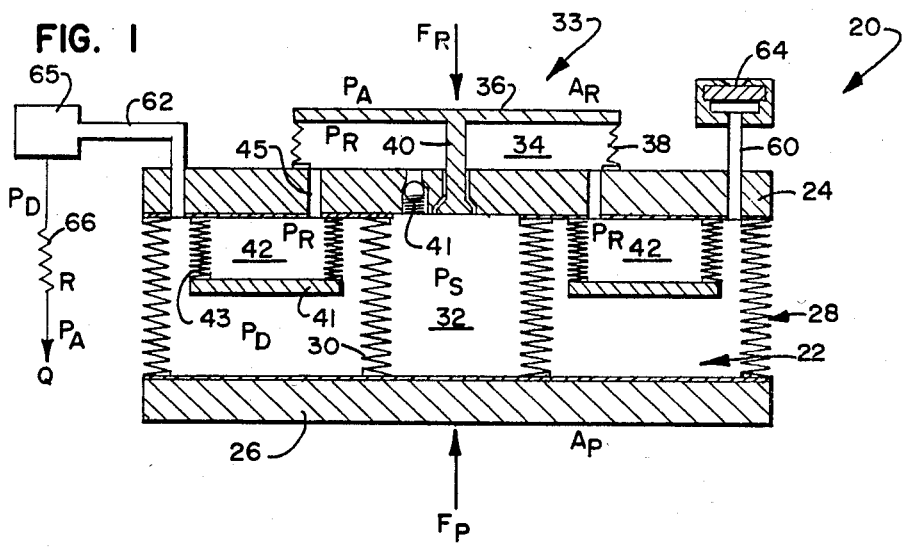
FIG. 1 is a diagrammatic/cross-sectional view of an embodiment of the present invention wherein the regulator compensates for atmospheric pressure.

Referring now to the drawings, there is illustrated in FIGS. 1 through 7 various embodiments of an implantable infusion pump in accordance with the principles of the present invention, the infusion pump being generally referenced by the reference numeral 20. The embodiment of the infusion pump 20 illustrated in FIG. 1 includes a variable volume drug chamber 22 formed by a wall structure 24 of the infusion pump 20 and a diaphragm 26 interconnected to the wall structure 24 by a spring arrangement 28. The spring arrangement 28 functions as a force producing ($F_p$) device causing the diaphragm 26 to exert a variable force on the drug solution in the drug chamber 22. It will be appreciated, that any other number of force producing devices might be used to exert a force on the drug solution. Interconnecting the wall structure 24 to the diaphragm 26 is a cylindrical column of under pressure fluid ($P_s$) enclosed by a flexible bellows arrangement 30 so as to form a support piston 32 which counters the force being exerted by the diaphragm 26 on the drug solution in the drug chamber 22. The support piston 32 is interconnected to a regulator apparatus 33 including a chamber 34 defined by a diaphragm 36 and force producing spring arrangement 38 which produces a predetermined force ($F_R$) on the diaphragm 36. The support fluid of the support piston is interconnected to the regulator chamber 34 by a one-way valve arrangement 40 which controls the fluid flow into the regulator chamber 34. It will be appreciated that the spring 38 can exert a variable force over a range of movement and still be used to provide a predetermined force, since in operation, the diaphragm 36 will move very little. The valve arrangement 40 will provide a steady, regulated flow. In the embodiment shown in FIG. 1, the support fluid of the support piston 32 is contained in the regulator chamber 34 and a chamber 42 interconnected to the chamber 34 by a pathway 45 and including a diaphragm 41 and bellows 43 arrangement, so as to be kept separate from the drug solution in the drug chamber 22. Additionally, the diaphragm 36 is exposed to the internal body pressure which reflects the atmospheric pressure. In this manner, the regulator 33 comprising diaphragm 36 and spring bellows 38 is referenced to atmospheric pressure and produces a constant flow rate regardless of atmospheric changes.

Figure 2:
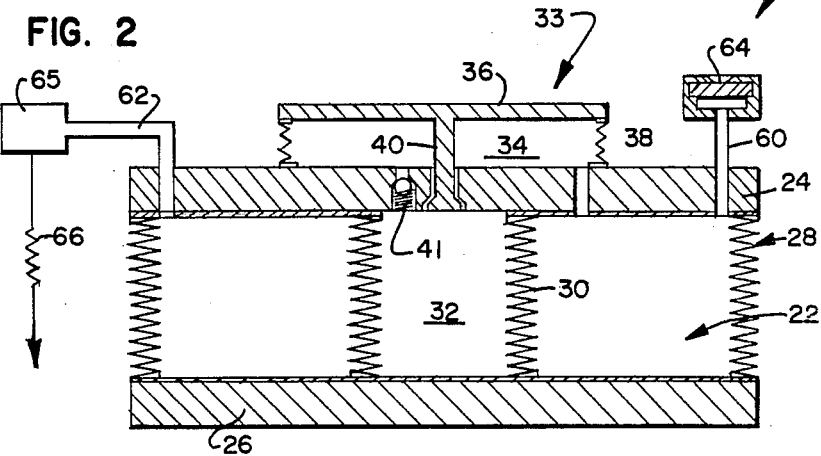
FIG. 2 is a diagrammatic/cross-sectional view of an embodiment of the present invention wherein the drug solution is used as the support fluid of the support piston.

The embodiment illustrated in FIG. 2 utilizes the drug solution as the support fluid for the piston 32 and thus does not include the fluid chamber 42. Since the drug solution itself is used as the support fluid in the support piston, it must pass through the regulator valve 40. This embodiment achieves a larger volumetric efficiency and a lower cost due to fewer parts compared to electronic or vapor pressure driven pumps. Moreover, the regulator diaphragm 36 is exposed to the external pressure as illustrated in FIG. 1.

Figure 3:
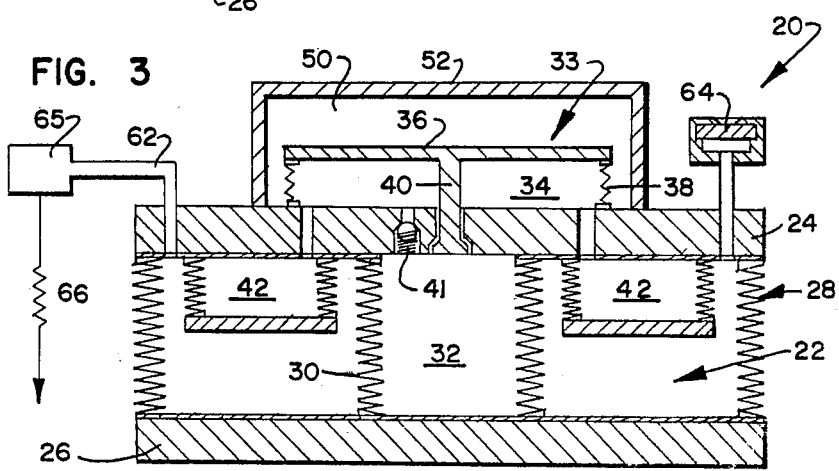
FIG. 3 is a diagrammatic/cross-sectional view wherein the regulator does not compensate for atmospheric pressure.

FIG. 3 illustrates an embodiment of the present invention wherein the regulator diaphragm 36 is internally referenced to a chamber 50 enclosed by an immovable shell structure 52, the chamber 50 being filled with gas at atmospheric pressure (or lower). This embodiment does not provide any reference to the atmospheric pressure and as a result, has to operate at a higher pressure in order to avoid variation in atmospheric pressure. This embodiment, as well as that shown in FIG. 4 which has the same closed chamber 50 but no support piston fluid reservoir 42, are designs that allow more freedom in construction since the small regulator mechanism can be placed in the pump interior with no connection to the exterior. It also provides a sealed place for electronic controls that can mechanically change the regulator pressure ($P_R$) or set point.

In the embodiments illustrated in FIG. 1 and FIG. 3, at the end of a cycle when the drug chamber 22 is empty, most of the operating fluid of the piston 32 will be transferred to the chamber 42. When drug solution is injected into the infusion pump through the refill septum, the pressure ($P_D$) in the drug chamber 22 will rise and the diaphragm 26 will retract producing negative pressure across the regulator 33. This excess negative drug pressure will cause the regulator 33 to close to allow the internal pressure to fall to the control point. In order to reset the infusion pump for another cycle, a bypass check valve 41 responds to the negative pressure and allows operating fluid to flow back into the support piston 32. When the infusion pump drug chamber if full, the regulator 33 takes over control of the drug chamber pressure as soon as a small amount of drug solution has left the drug chamber.

Figure 4:
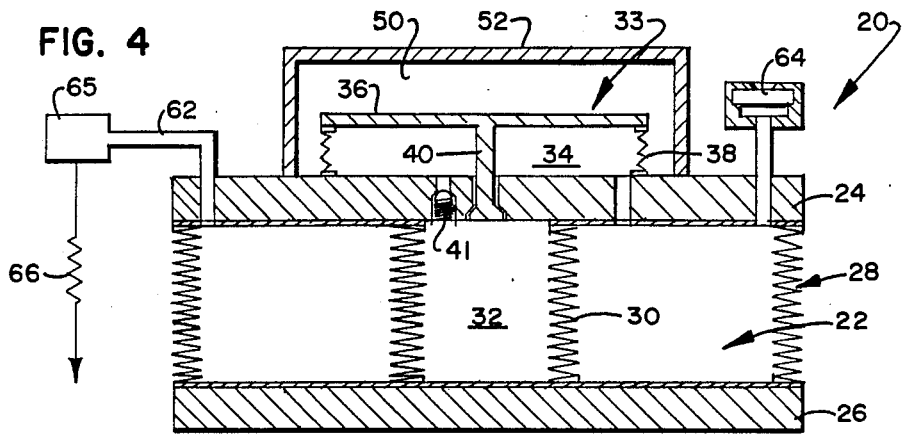
FIG. 4 is a diagrammatic/cross-sectional view of an embodiment of the present invention wherein the regulator does not compensate for atmospheric pressure and the drug solution serves as the support fluid for the support piston.
Figure 5:
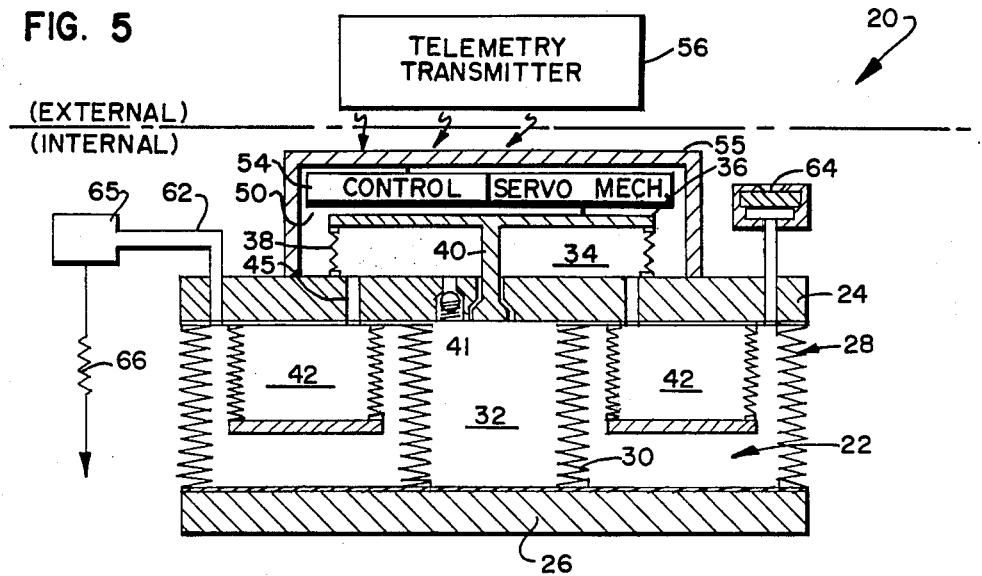
FIG. 5 is a diagrammatic/cross-sectional view illustrating an electronically controlled embodiment of the present invention.

In the embodiment illustrated in FIGS. 2 and 4, the drug solution itself refills the support piston chamber, through the check valve. The embodiment illustrated in FIG. 5 illustrates an electronically controlled version of an infusion pump in accordance with the principles of the present invention. In the air space in the chamber 50 behind the regulator diaphragm 36 there are placed conventional telemeter receiver controlling circuits 54 for receiving commands from a telemetry transmitter 56 and for controlling small electromechanical components or servomechanisms 55 that can vary the force exerted on the diaphragm 36 and thus vary the regulator reference pressure. It will be appreciated that any number of well known devices might be utilized. For example, this might be in the form of a small electric motor and gear train that would compress or expand the spring arrangement 38 supplying the force on the diaphragm 36. Battery power would be required only when the settings were changed. The telemetry transmitter and receiver could be of the type presently used for transcutaneous signal transmission and are available commercially. Examples of such control circuitry are disclosed in U.S. Pat. Nos. 4,373,527 and 4,146,029. Signal coding could be used to decrease the possibility of accidental operation. The receiver controls might be passive circuits that obtain their power from the transmitter since they would be activated only to change the pressure.

The regulator of the present invention is particularly suited to changing the reference pressure set point slowly due to the slow flow rate out of the infusion pump, and rapid changes in drug solution flow rate are not particularly suited for this design. The pressure control circuit would preferably be in the form of an adjustable basal rate rather than the flexible control used in other pumps that can be used to deliver fast bolus flows. This slow control greatly increases the safety of its operation.

Figure 6:
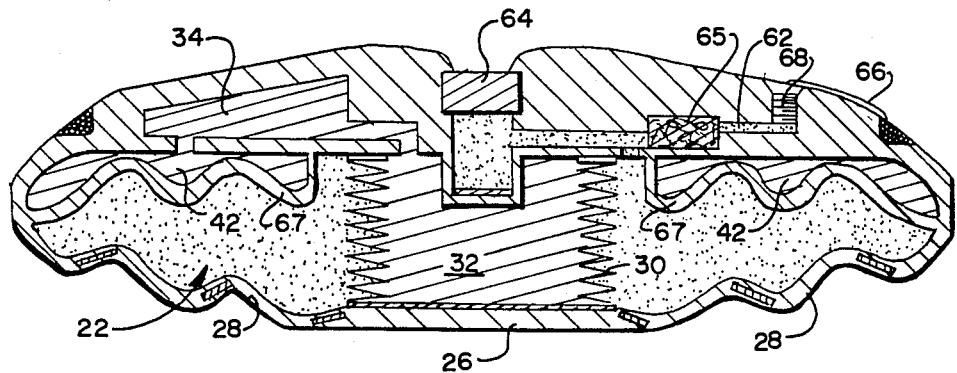
FIG. 6 is a diagrammatic/cross-sectional view illustrating a possible packaging arrangement of components of an embodiment of an infusion pump in accordance with the principles of the present invention.

The most compact design of an infusion pump of the present invention uses the outer shell structure of the unfusion pump as a spring element that stores energy in the form of tension and compression of the metal or plastic material comprising the shell structure. The reference pressure for the regulator can be obtained from either the top or bottom of the pump in the form of a thin, large diameter diaphragm that separates the pressure transmitting fluid from the body tissue. FIG. 6 illustrates a possible packaging of the components of the embodiment illustrated in FIG. 3.

As with other infusion pumps, such as U.S. Pat. No. 3,731,681, hereby incorporated by reference, the present invention will include an inlet port 60 and an outlet port 62. Suitably positioned in the inlet port 60 is a self-sealing, penetrable septum member 64, a filter 65 being positioned in the outlet port. A capillary flow restricter 66 is interconnected to the outlet port by a suitable connector 68. The capillary flow restrictor might then be interconnected to a catheter for delivery of the drugs to an infusion site in the body although any number of other well known devices might be used. A convoluted diaphragm 67 is utilized to allow nesting of the drug chamber diaphragm 26 therewith. (In this illustration, the regulator 34 is generally illustrated without any of its individual components.)

Figure 8:
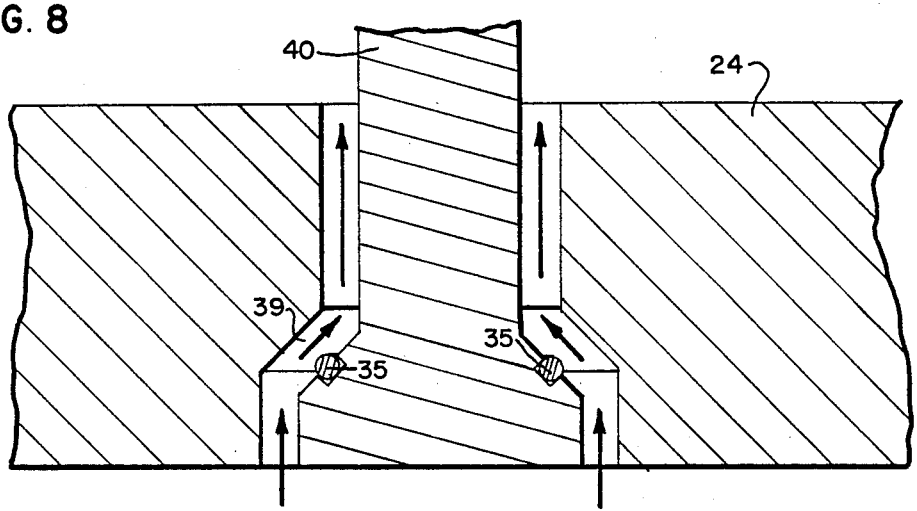
FIG. 8 is an enlarged partial sectional view of the regulator valve in an increased flow setting.
Figure 9:
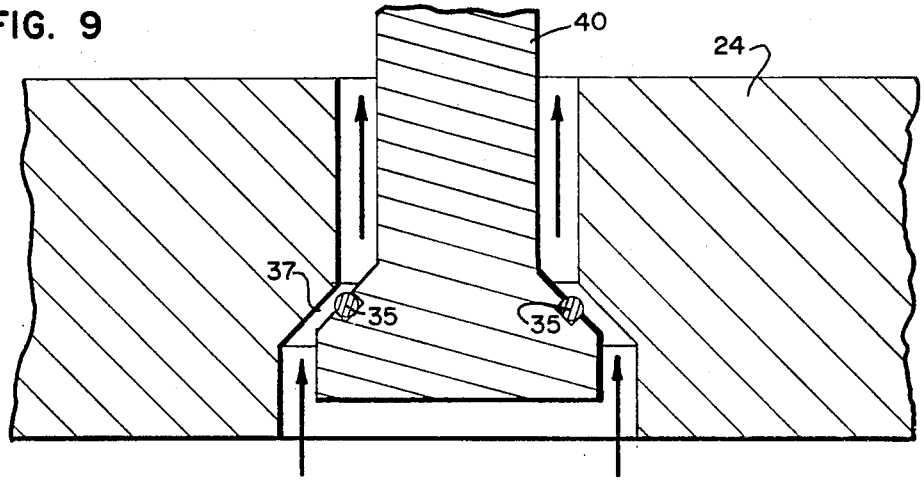
FIG. 9 is a view similar to FIG. 8 wherein the regulator valve is in a reduced flow setting.

The total force on the diaphragm 26 is opposed by the sum of the drug solution pressure in the drug chamber 22 and the support piston 32 fluid pressure:

$$F_p + (P_A A_p) = (P_s A_s) + (P_D A_D)$$

wherein;
$F_p$ = spring force of diaphragm
$P_A$ = pressure of atmosphere
$A_p$ = area of diaphragm 26
$P_s$ = pressure of fluid in support piston
$A_s$ = area of support piston diaphragm
$P_D$ = pressure in drug chamber
$A_D$ = area of drug chamber diaphragm Regulation of the drug solution pressure ($P_D$) occurs due to mechanical negative feedback action of the valve 40 so as to maintain a balanced force on the diaphragm 36. If the pressure ($P_D$) of the drug solution drops, so does the regulator pressure ($P_R$) which causes the valve 40 to open to allow entry of more of the fluid from the support piston chamber which is at a high pressure ($P_s$). This is illustrated in FIG. 8 wherein the valve 40 provides a larger opening 39 so as to allow more of the support solution in the support piston 32 to flow into the regulator reservoir 34. FIG. 9 illustrates the valve 40 in a reduced flow setting wherein a smaller opening 37 is provide for drug solution flow. As illustrated in FIGS. 8 and 9, the valve 40 will preferably include a seal 35, such as an O-ring or the like. This restores the balance forces on the regulation diaphragm 36 by increasing regulator pressure ($P_R$). The control equations are:

$$P_R A_R - P_A A_R = F_R$$

wherein;
$P_R$ = pressure in regulation chamber
$A_R$ = area of regulator diaphragm
$P_A$ = pressure of atmosphere
$F_R$ = spring force on regulator diaphragm The fluid storage chamber 42 has a soft bellows so the pressure ($P_D$) is about equal to ($P_R$). Therefore, the drug chamber pressure can be expressed as:

$$P_D A_R - P_A A_R = F_R$$

Solving for $P_D$:

$$P_D = F_R/A_R + P_A$$

The flow through the capillary tube 66 is expressed in terms of the pressure difference across it divided by the fluid resistance:

$$Q = (P_D - P_A/R)$$

wherein;
Q=flow in volume per unit time
R=fluid resistance of capillary
Solving for Q putting in terms for the pressure $P_D$:

$$RQ = P_D - P_A = F_R/A_R + P_A - P_A$$

The two terms for atmospheric pressure cancel to give:

$$Q = F_R/A_R R$$

Figure 7:
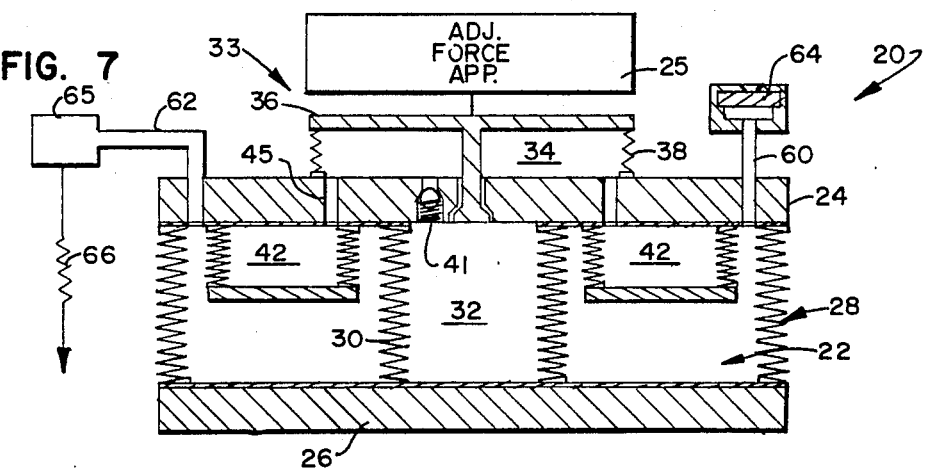
FIG. 7 is a diagrammatic/cross-sectional view of an embodiment of the present invention which utilizes an adjustable force applicator device for varying the reference pressure of the regulator.

The regulator force ($F_R$), the regulator diaphragm area ($A_R$) and the capillary resistance R are fixed quantities, therefore, the flow Q will be fixed independent of the atmospheric pressure and the force on the drug chamber diaphragm 26. In a non-electronically controlled version of the infusion pump, the regulator force ($F_R$) might be preset by selecting a spring member 38 which creates the required force ($F_R$). In FIG. 7, another embodiment is illustrated wherein an adjustable force applicator 25 is utilized to apply a predetermined force ($F_R$) on the diaphragm 36.

It is to be understood that even though the above numerous characteristics and advantages of the invention have been set forth in the foregoing description, together with details of the structure and function of the invention, the disclosure is illustrated only, and changes may be in detail, especially in matter of shape, size and arrangement of parts with the principles of the invention to the full extent indicated by the broad general meaning of the terms in which the appended claims are expressed.

What is claimed is:

1. An infusion pump for implantation in a living body, comprising:
    (a) a housing having a variable volume, drug chamber for holding a drug solution;
    (b) outlet port means for conducting the drug solution from the drug chamber to a first site outside the housing;
    (c) inlet port means for introducing the drug solution into the drug chamber from a second site outside the housing;
    (d) force means including a diaphragm for exerting a force on the drug solution in the drug chamber;
    (e) fluid piston means for opposing the force exerted by the diaphragm of the force means on the drug solution; and
    (f) regulator means for regulating the pressure of the fluid of the piston means such that a constant total force is exerted on the drug solution in the drug chamber.

2. An infusion pump in accordance with claim 1, wherein the housing includes an external wall structure, a first portion of the external wall structure being substantially rigid, the force means including movable spring diaphragm means forming a second portion of the external wall structure.

3. An infusion pump in accordance with claim 1, wherein the diaphragm forms an external wall portion of the housing so as to be subjected to the internal body pressure.

4. An infusion pump in accordance with claim 3, wherein the diaphragm includes a plurality of conical spring sections integral therewith.

5. An infusion pump for implantation in a living body, comprising:
    (a) a housing having a variable volume drug chamber for holding a drug solution;
    (b) outlet port means for conducting the drug solution from the drug chamber to a first site outside the housing;
    (c) inlet port means for introducing the drug solution into the drug chamber from a second site outside the housing;
    (d) first diaphragm means for exerting a force on the drug solution in the drug chamber; and
    (e) regulator means for regulating the pressure of the drug solution, the regulator means including fluid piston means including a column of pressurized fluid for opposing the force of the first diaphragm means and second diaphragm means exerting a predetermined force on a second chamber of the housing so as to provide a reference pressure, the second chamber being in fluid communication and interconnected to the fluid piston means by one-way valve means for regulating fluid flow from the fluid piston means to the second chamber whereby a constant total force is exerted on the drug solution of the drug chamber, the fluid pressure of the second chamber corresponding to the fluid pressure of the drug chamber.

6. An infusion pump in accordance with claim 5, wherein the fluid of the second chamber and the fluid piston means is maintained separate from that of the drug solution.

7. An infusion pump in accordance with claim 5, wherein the fluid of the fluid piston means is the drug solution itself.

8. An infusion pump in accordance with claim 5, wherein the second diaphragm is enclosed by a rigid outer shell such that the force exerted by the second diaphragm on the second chamber remains constant regardless of atmospheric pressure changes.

9. An infusion pump in accordance with claim 5, wherein the second diaphragm is exposed to internal body pressure such that the force exerted by the second diaphragm on the fluid of the second chamber reflects changes in atmospheric pressure.

10. An infusion pump in accordance with claim 5, wherein the reference pressure of the regulator means is electronically controlled.

11. An infusion pump in accordance with claim 5, wherein the regulator means is programmable so as to provide for varying the reference pressure and predetermined times.

12. An infusion pump for implantation in a living body, comprising:

(a) a housing having a first wall portion and a second wall portion defining a variable volume drug chamber for holding the drug solution;

(b) outlet port means for conducting the drug solution from the drug chamber to a first site outside the housing;

(c) inlet port means for introducing the drug solution into the drug chamber from a second site outside the housing;

(d) force means for forcing the second wall portion toward the first wall portion whereby the drug solution in the drug chamber is placed under pressure;

(e) regulator means for regulating the pressure of the drug solution in the drug chamber, and thus the infusion rate of the drug solution into the body, the regulator means including fluid piston means interconnecting the first and second wall portions of the housing and including an enclosed column of fluid under pressure for opposing the force exerted by the second wall portion, the regulator means further including a regulator chamber in fluid comminucation with, and interconnected to, the fluid piston means by one-way valve means for allowing fluid flow from the fluid piston means into the regulator chamber, the regulator chamber being operatively interconnected to the drug chamber such that the pressure of the fluid in the regulator chamber and the drug solution pressure correspond, the regulator means being operated on by reference force means defining the operational drug solution pressure of the infusion pump.

13. An infusion pump in accordance with claim 12, wherein the reference force means is adjustable.

14. An infusion pump in accordance with claim 12, including electronic receiver means for receiving control signals transmitted from a location exterior of the body, the electronic receiver means being operatively interconnected to means for varying the reference force whereby the infusion rate of the implantable infusion pump can be electronically controlled.

15. An infusion pump in accordance with claim 12, wherein the housing includes an external, flexible wall portion formed in part by the second wall portion.

16. A method of infusing fluids into a living body, the method comprising the following steps:

a. implanting a self-powered infusion pump including a variable volume drug chamber into a living body, an inlet port leading to a variable volume drug chamber of the infusion pump;

b. interconnecting an outlet port to at least one infusion site in the body;

c. injecting drug solution through skin of the body and through a self-sealing, penetrable member positioned in the inlet port to fill the drug chamber; and d. exerting a cumulative force on the drug solution in the drug chamber corresponding to the total force exerted by a first diaphragm means on the drug solution and an imposing force exerted by fluid piston means whose fluid pressure is controlled by pressure regulator means operatively interconnected to the fluid piston.

* * * * *

UNITED STATES PATENT AND TRADEMARK OFFICE
CERTIFICATE OF CORRECTION

PATENT NO. : 4,718,893

DATED : Jan. 12, 1988

INVENTOR(S) : Dorman et al.

It is certified that error appears in the above-identified patent and that said Letters Patent is hereby corrected as shown below:

Column 1, line 44, "diaphram" should be --diaphragm--.

Column 1, line 46, "atmostpheric" should be --atmospheric--.

Column 1, line 51, "Adminisistration" should be --Administration--.

Column 1, line 64, "Conge" should be --Congo--.

Column 2, line 37, "restrictions" should be --restrictors--.

Column 2, line 66, "programed" should be --programmed--.

Column 3, line 66, "constanc" should be --constant--.

Column 4, lines 38 and 39, "expell" should be --expel--.

Column 8, line 5, "unfusion" should be --infusion--.

Column 8, line 21, "restricter" should be --restrictor--.

Column 9, line 44, "illustrated" should be --illustrative--.

Signed and Sealed this

Thirteenth Day of September, 1988

*Attest:*

DONALD J. QUIGG

*Attesting Officer*  *Commissioner of Patents and Trademarks*